United States Patent [19]

Jubin

[11] 4,128,587

[45] Dec. 5, 1978

[54] MANUFACTURE OF TERTIARY BUTYL HYDROPEROXIDE

[75] Inventor: John C. Jubin, Wallingford, Pa.

[73] Assignee: Atlantic Richfield Company, Los Angeles, Calif.

[21] Appl. No.: 745,142

[22] Filed: Nov. 26, 1976

[51] Int. Cl.$^2$ .......................................... C07D 179/02
[52] U.S. Cl. .................................................. 568/571
[58] Field of Search ........................ 260/610 B, 610 A

[56] References Cited

U.S. PATENT DOCUMENTS

| 2,733,270 | 1/1956 | Fisher | 260/604 R |
| 2,845,461 | 7/1958 | Winkler et al. | 260/610 B |
| 3,907,902 | 9/1975 | Crane | 260/610 B |
| 3,987,115 | 10/1976 | Zajauk et al. | 260/631 R |

*Primary Examiner*—James O. Thomas, Jr.
*Assistant Examiner*—Werren B. Lone
*Attorney, Agent, or Firm*—John R. Ewbank

[57] ABSTRACT

The concentration of tertiary butyl alcohol in the isobutane feed to a reactor for the preparation of tertiary butyl hydroperoxide is controlled to be within the range from about 10% to about 30% whereby the conversion and selectivity and reaction rates provide advantageous results.

4 Claims, No Drawings

MANUFACTURE OF TERTIARY BUTYL HYDROPEROXIDE

BACKGROUND OF INVENTION

1. Field of Invention

This invention relates to a method for increasing the selectivity of a liquid phase oxidation of isobutane with molecular oxygen for the production of tertiary butyl hydroperoxide.

2. Prior Art

Winkler et al U.S. Pat. No. 2,845,461 describes the preparation of tertiary butyl hydroperoxide by the oxidation of liquid isobutane with molecular oxygen at 200°–300° F. at a pressure exceeding 400 psig.

Grane U.S. Pat. No. 3,907,902 describes the liquid phase oxidation of isobutane at 200°–300° F. at 300–700 psig using a feed containing 0.2 to 3% of isopropyl alcohol, isobutyl alcohol or secondary butyl alcohol. Said Grane patent explains that small amounts of tertiary butyl alcohol, such as up to 3% of tertiary butyl alcohol "gives substantially no improvement in the selectivity of reaction toward the production of tertiary butyl hydroperoxide."

Said Grane patent explains that the liquid oxidate (after removal of unreacted isobutane or IB) contains Tertiary Butyl Hydroperoxide (or TBHP) and Tertiary Butyl Alcohol (or TBA) as the principal components. As the selectivity for TBHP decreases, larger amounts of TBA are found in the oxidate. The selectivity for TBHP is decreased by increasing residence time and/or temperature. Increasing the residence time in the reactor increases the extent of conversion of the IB. Hence maintaining uniform residence time in a series of tests eliminates the effect of this highly important variable. A relatively small change in temperature, while retaining a uniform residence time in a series of tests, provides a measurable change in selectivity as well as a measurable change in conversion.

It is convenient to employ the same pressure throughout a series of comparative runs, but the effect, if any, of pressure on selectivity and/or conversion is relatively small compared to the significant effects of temperature. The pressure must be sufficient to maintain liquid phase conditions, and desirably is as high (while still being under a safety limit of about 1,000 psig) as economically tolerable. Thus laboratory tests can conveniently be conducted at higher pressures (e.g. 800 psig) than would be used industrially.

Heretofore there have been a variety of studies of the chronology of the liquid phase oxidation of isobutane so that there has long been a recognition of the propensity of tertiary butyl hydroperoxide to be somewhat autocatalytic. That is, as more tertiary butyl hydroperoxide is formed during the oxidation of isobutane, the presence of such tertiary butyl hydroperoxide tends to accelerate the reaction rate, serving like a catalyst for more rapid conversion of additional isobutane, but with the formation of larger amounts of byproduct tertiary butyl alcohol. Relatively large proportions of TBA are formed when most of the isobutane is converted at an elevated temperature. The relative proportion of TBA formation increases when there are incremental increases in the TBHP product concentration at such elevated temperature high conversion conditions. Hence, it is sometimes appropriate to control both the residence time and the temperature of the isobutane oxidation so that about 20–40% of the isobutane is converted prior to the separation of the reaction product for the recycling of the isobutane and for the separation of the liquid oxidate. Said Winkler et al patent describes and claims selectivities of about 50 mol percent. As the selectivity for TBHP is increased, the concentration of TBA in a Winkler type oxidate is decreased.

The market for tertiary butyl alcohol has long been complicated by the availability of a few outlets at prices which were attractively high, but which were also relatively small volume markets and not readily susceptible of expansion. A large market for isobutyl alcohol in fuel oil or in other liquid fuels has long existed, but the price at which tertiary butyl alcohol can be sold as fuel has ordinarily been relatively unattractive. In recent years, a considerable portion of the tertiary butyl alcohol byproduct from processes involving TBHP has been disposed of in gasoline at a price significantly less than would be expected for a chemical having the unique advantages of tertiary butyl alcohol.

A high price and a relative scarcity of isobutane has resulted from the complicated changes in the petrochemical marketing of recent years. The supply and demand factors have been such that there have been periods and localities in which there appeared to be incentives for the conversion of tertiary butyl alcohol to isobutylene and the hydrogenation of isobutylene to isobutane for recycling through the reactor for the formation of tertiary butyl hydroperoxide. Such conversion of TBA to IB permits a plant to market propylene oxide as its sole product and to generally ignore some of the fluctuations in the demand or price for TBA. The selectivity of the oxidation step for preparing larger amounts of tertiary butyl hydroperoxide and relatively smaller amounts of tertiary butyl alcohol is always important, but can be emphasized when costs are considered for a process in which the tertiary butyl alcohol is recycled by the steps of dehydration followed by hydrogenation. The fluctuating market price of tertiary butyl alcohol reflects both its utility as a special chemical and its utility as a component of gasoline.

There are important advantages to preparing propylene oxide by the use of tertiary butyl hydroperoxide as an intermediate. Such propylene oxide production must compete, however, with methods for preparing propylene oxide by the chlorohydrin method or by procedures using ethyl benzene hydroperoxide and/or other materials for which the market for the coproduct may be more attractive than is the established market for tertiary butyl alcohol.

During the more than a decade since the filing of the application maturing as said Winkler patent, there has been a continuing demand for improvements in the selectivity for the reaction of IB for the formation of TBHP, but the technologists and engineers have been unable to achieve as high selectivity for TBHP as for some other tonnage chemicals.

SUMMARY OF THE INVENTION

In accordance with the present invention, the selectivity for the formation of tertiary butyl hydroperoxide is enhanced by providing tertiary butyl alcohol in a concentration of from about 10% to about 30% in the liquid feed (predominantly isobutane) supplied to the reactor for the preparation of tertiary butyl hydroperoxide.

The invention is further clarified by reference to a plurality of examples.

EXAMPLE 1

Commerical production of TBHP is usually conducted in a continuous reactor requiring a significant capital investment by reason of the pressure, temperature, slow throughput, desirability for control of flow of liquid, desirability for control of flow of gas, and other factors generally unique (amongst tonnage chemicals) for TBHP.

It is possible to employ one form of laboratory reactor consisting of a large pressurized kettle in which a stirrer maintains a reasonably uniform mixture while liquid feedstock is injected into such reaction mixture and a stream of the reaction mixture is withdrawn from a zone different from the feedstock injection zone. A liquid level control can maintain the amount of liquid in the autoclave at a predetermined height so that the rate of removal of reaction mixture responds to the combination of factors comprising reaction rate and feedstock injection rate. Air is injected into the liquid to oxidize components, thereby forming a nitrogen-containing effluent gas. A reflux condenser desirably is positioned between the autoclave and the gas pressure regulator so that all of the gas withdrawn from the regulator is relatively free of hydrocarbons (most notably isobutane) which may be vaporized. The gaseous effluent from the autoclave (via reflux condenser) can go through a pressure regulator maintaining the autoclave at a predetermined elevated pressure. A pressure of 800 psig was used in the described experimental work, but a wider pressure range can be operable without departing from the published literature concerning pressures useful in preparation of TBHP. A pressure in the lower pressure range (e.g. 300–500 psig) might be used in commercial operations for economic reasons. Previous work has shown that the effect of pressure on the reaction rate is not significant. The present invention notes the necessity of liquid phase operation and the necessity of an elevated pressure to maintain such liquid phase, but does not stress the amount of pressure other than illustrating the 300–800 psig range as appropriate.

Pilot plant equipment intended to have plausible resemblence to commercial operations is costly to build, costly to start up and expensive to operate, thus stimulating interest in obtaining the maximum useful data from the minimum number of runs.

In the research facility, a stirred kettle type of autoclave was operated to permit continuous injection of feedstock and to permit continuous, but controlled withdrawal of the liquid contents from the reactor for maintaining the desired level of liquid. Such research apparatus was provided with pumps for injecting liquid feedstock, valves for withdrawing liquid from the reactor, provision for injecting an oxygen-containing gas, pressure regulated valves for withdrawing gaseous effluent, and heat exchange systems for regulating the temperature of the liquid reaction mixture during its several hours residence in the reactor. After a set of adjustments had been made, the process could be operated for days with reliable maintenance of a uniform residence time.

Because the desired reaction should occur in the absence of metallic ions, which accelerate the decomposition of TBHP, all components of the pumps, reactor and recovery system must be carefully selected to provide such a contaminant-free environment.

A series of tests were conducted while maintaining a uniform liquid residence time. The control of the liquid level in the reactor helped to maintain such constant residence time. In a control test, the temperature was maintained at 270° F. with the pressure maintained at 800 psig. The kettle type autoclave had a liquid level control adapted to maintain a constant liquid level by continuously withdrawing liquid contents from the reactor with constant hydrocarbon feed rate to the reactor. In the control test pure 100% isobutane was the feedstock, and, 23.2% of the isobutane was converted, and 76.8% of the isobutane feed was recovered in the liquid effluent from the reactor. The tertiary butyl alcohol was 38.9% of the liquid oxidate (mixture of TBHP and TBA) in such control, thus providing a TBHP selectivity of 61.1 weight percent. Such selectivity of the control herein is significantly superior to the approximately 46% selectivity disclosed in Example 1 of Winkler et al U.S. Pat. No. 2,845,461 for the similar conversion at 257° F. notwithstanding the use herein of a temperature 13° F. higher than Winkler et al.

In accordance with the present invention, a feedstock mixture consisting of 20% by weight TBA and 80% isobutane was fed to the same stirred, pressurized kettle at 270° F. at 800 psig. The mol percentages in the feedstock are about 83.6% isobutane and about 16.4% TBA. The feedstock mixture was injected into the reaction mixture and liquid reactor contents were withdrawn at a rate for maintaining the same constant residence time and the same liquid level as in the control test. This preparation of TBHP, in accordance with the present invention, was regulated to be closely similar to said control test except for the use of TBA in the feedstock. In both cases, air was injected into the liquid contents of the reactor with unreacted oxygen and nitrogen withdrawn from the reflux condenser. The results obtained from both tests are shown in Table 1.

TABLE 1

| Effect of TBA Dilution of $IC_4$ Feed for TBHP Preparation | Control | Ex. 1 | Difference |
|---|---|---|---|
| Experimental Conditions | | | |
| Reactor Temperature, ° F. | 270 | 270 | None |
| Reactor Pressure, psig | 800 | 800 | None |
| Liquid Feedstock Composition | | | |
| $IC_4$, as Wt. % of Liquid Feed | 100 | 80 | − 20 |
| TBA, as Wt. % of Liquid Feed | None | 20 | + 20 |
| Isobutane Conversion | | | |
| Conversion, as Wt. % of $IC_4$ in Feed | 23.2 | 17.5 | − 5.7 |
| Conversion, as Wt. % of Liquid Feed | 23.2 | 14.0 | − 9.2 |
| TBHP Production | | | |
| Selectivity, as Wt. % of TBHP formed per wt. of oxidate formed | 61.9 | 79.2 | + 17.3 |
| Yield, as Wt. % of Liquid Feed | 20.6 | 16.4 | − 4.2 |

At constant operating conditions, the effect of diluting the isobutane feed with 20 weight percent TBA is summarized as follows:

Both isobutane conversion and TBHP yield are decreased as a result of the dilution of the reactor contents with the TBA contained in the feedstock. This was anticipated and may reasonably by predicted by the reaction kinetics thought to describe this system where both isobutane conversion and TBHP formation decrease as the isobutane and TBHP concentrations in the reactor are reduced (through TBA dilution).

However, the absolute difference of 17.3% in selectivity to TBHP amounts to a 30% improvement based upon the 61.1% selectivity obtained in the control. A selectivity increase of 30% could not have been predicted through reaction kinetics on the basis of a plausible reduction in isobutane conversion and/or on the basis of a plausible dilution of the reactor contents with TBA. The results shown in Table 1 are surprising and unobvious to technologists familiar with TBHP literature.

Because the market for TBHP and products (e.g. propylene oxide) derived therefrom can be profitable and because the market for TBA is sometimes quite depressed, the selectivity for TBHP is among the most important characteristics of an isobutane oxidation reaction. For a reaction conducted at the same space rate, same pressure and same temperature, the one producing the least TBA and having the highest selectivity for TBHP is ordinarily preferred during periods when it is difficult to sell TBA at a price appropriate for such a unique chemical.

EXAMPLE 2

In the preparation of TBHP, the oxidation reaction by which isobutane is consumed is very sensitive to the temperature at which it takes place. The reaction rate increses significantly with increases of temperature. Although the temperature of 275° F. is close to the 270° F. of Example 1, the reaction rate for oxidation of isobutane is measurably faster. Moreover, the increased temperature favors greater production of TBA and lower selectivity for TBHP. Data relating to the preparation of TBHP at 275° F. are shown in Table 2.

TABLE 2

| Effect of TBA Dilution of IC$_4$ Feed for TBHP Preparation | Control | Ex. 2 | Difference |
|---|---|---|---|
| Experimental Conditions | | | |
| Reactor Temperature, ° F. | 270 | 275 | + 5 |
| Reactor Pressure, psig | 800 | 800 | 0 |
| Liquid Feedstock Composition | | | |
| IC$_4$, as Wt. % of Liquid Feed | 100 | 80 | − 20 |
| TBA, as Wt. % of Liquid Feed | None | 20 | + 20 |
| Isobutane Conversion | | | |
| Conversion, as Wt. % of IC$_4$ in Feed | 23.2 | 26.1 | + 2.9 |
| Conversion, as Wt. % of Liquid Feed | 23.2 | 20.9 | − 2.3 |
| TBHP Production | | | |
| Selectivity, as Wt. % of TBHP formed per Wt. of Oxidate formed | 61.1 | 69.9 | + 8.8 |
| Yield, as Wt. % of Liquid Feed | 20.6 | 21.2 | + 0.6 |

The data at 275° F. demonstrate that TBHP yield can be substantially restored (relative to control) with an absolute increase of 8.8% in TBHP selectivity. This amounts to a 14% improvement relative to the 61.1% selectivity obtained in the control when calculations are based upon efficient utilization of scarce isobutane. Example 2 indicates that by appropriate control of all reaction parameters, undesired isobutane consumption to produce TBA byproduct can be reduced by 10% (relative to control), while the desired reactions to yield TBHP can be maintained. There was no adequate basis for predicting such unobvious and unexpected results achieved through the use of TBA diluent and increased temperature on the basis of the literature with which TBHP technologists have been familiar.

EXAMPLE 3

By a series of tests, it is established that TBA, in an appropriate range of concentrations, is significantly advantageous as a feedstock component in producing TBHP by oxidation of isobutane. The diluent has some propensity to decrease yield and to decrease the conversion of the isobutane. However, adequate yields of TBHP are attainable by small increases in reactor temperature with a net reduction in isobutane consumption and a net increase in TBHP production per day from a given volume of reactor.

Only when the TBA concentration is at least 10% by weight does the selectivity effect become significant enough to justify the costs inherent in recycling TBA through the pressurized reactor. If the TBA concentration in the feedstock significantly exceeds 30% by weight, the need for raising reaction temperature to maintain yield is excessive. Good results are obtained in the concentration range from 10% to 30%, preferably about 20%. The temperature must be within the 250°–300° F. range at a pressure exceeding 300 psig and maintaining liquid phase conditions.

EXAMPLE 4

The kettle type autoclave of Example 1 is employed for preparing TBHP by the oxidation of IB at 800 psig with the flow control system adjusted to maintain the uniform residence time of Example 1, while supplying a liquid feedstock consisting of 12% TBA and 88% IB. The oxidation is conducted at 280° F. providing a yield of TBHP greater than the control of Example 1. However, in a control using only 3% TBA and 97% IB as the liquid feed, the TBHP yield is unsatisfactory and formation of byproducts comprising organic acids and TBA at the 280° F. and related process conditions are significantly greater than when the TBA concentration is 12% in accordance with the present invention.

EXAMPLE 5

A liquid feed consisting of 28% TBA and 72% IB is oxidized at 285° F. and 800 psig for the uniform residence time of Example 1 in the apparatus of Example 1. Advantageous selectivities for TBHP and low incremental production of TBA for 285° F. are contrasted with the unfavorable yields when oxidizing a mixture of 40% TBA and 60% IB at the same conditions.

In the seventh paragraph relating to the Prior Art, supra, it is explained that tertiary butyl alcohol, formed as the by-product from the utilization of tertiary butyl hydroperoxide as an oxidant, can be dehydrated to isobutene and the isobutene can be hydrogenated to isobutane, which can be recycled to the reactor. The method of the present invention can be utilized in a method in which the tertiary butyl hydroperoxide is employed as an oxidant to produce an oxidized product plus tertiary butyl alcohol, and such tertiary butyl alcohol, together with the tertiary butyl alcohol formed as a product in such oxidate is dehydrated to isobutene, and the thus-formed isobutene is hydrogenated to isobutane, and the thus prepared isobutane is recycled to the reactor to maintain the two-component composition of the feedstock to consist of 70%–90% isobutane and 10%–30% tertiary butyl alcohol.

I claim:

1. In the method in which a liquid feedstock containing a major amount of liquid isobutane is oxidized continuously by an oxygen-containing gas in a reactor of a predetermined size at a pressure maintaining isobutane in liquid phase, said pressure being within a range from 300 to 1000 psig, at a temperature within a range from about 250° F. to about 300° F. in an oxidation zone to produce continuously a liquid effluent from said reactor, processing said reactor effluent to separate unreacted isobutane and to separate a liquid oxidate containing tertiary butyl hydroperoxide from said reactor effluent, and recovering continuously a product containing tertiary butyl hydroperoxide from said method, the improvement which consists of:

employing as the liquid feedstock for said continuous method a mixture consisting of from 70% to 90% isobutane and an amount of tertiary butyl alcohol constituting from 10% to 30% by weight of said feedstock;

said tertiary butyl alcohol in said feedstock enhancing the rate of production of tertiary butyl hydroperoxide in said reactor of a predetermined size so that the rate of tertiary butyl hydroperoxide production assuredly measures greater than the rate of tertiary butyl hydroperoxide production measured at conditions in the absence of said tertiary butyl alcohol in the feedstock and said tertiary butyl alcohol in said feedstock enhancing the selectivity for the formation of tertiary butyl hydroperoxide in said oxidation zone, so that the quantity of tertiary butyl hydroperoxide relative to tertiary butyl alcohol formed in said liquid oxidate assuredly measures significantly greater than the quantity of teritary butyl hydroperoxide measured in a liquid oxidate obtained at corresponding conditions in the absence of said tertiary butyl alcohol in the feedstock.

2. The method of claim 1 in which the concentration of tertiary butyl alcohol in the liquid feedstock is within a range from about 12% to about 28%.

3. The method of claim 1 in which the concentration of tertiary butyl alcohol in the liquid feedstock is about 20%.

4. The method of claim 1 in which the temperature is about 275° F.

* * * * *